United States Patent [19]

Parnagian

[11] Plant 4,084

[45] July 26, 1977

[54] NECTARINE TREE

[76] Inventor: Sam Parnagian, 410 E. Adams, Fowler, Calif. 93625

[21] Appl. No.: 715,339

[22] Filed: Aug. 18, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A nectarine tree of vigorous growth and large size which bears early ripening, clingstone, yellow-fleshed fruit which ripens 10 to 14 days earlier than that borne by the Armking Nectarine Tree (U.S. Plant Pat. No. 2,943) of which it is a sport, and which is more highly colored than that borne by the Mayred Nectarine Tree (U.S. Plant Pat. No. 2,758).

1 Drawing Figure

BACKGROUND OF THE VARIETY

The present invention relates to a new and distinct variety of nectarine tree broadly characterized by its large size and vigorous growth and its bearing of early ripening, clingstone, yellow-fleshed fruit and more particularly to such a nectarine tree characterized by its bearing fruit which is more highly colored than that of the Mayred Nectarine Tree and, especially by the ripening of fruit 10 to 14 days earlier than that of the Armking variety which it most nearly resembles.

ORIGIN AND ASEXUAL REPRODUCTION OF THE NEW VARIETY

My new variety of nectarine tree was discovered by me in 1973 as a sport growing in an orchard of Armking nectarine trees owned by Denken Farms, a partnership of which I am a general partner. Such orchard is located near the City of Fowler, in the County of Fresno, in the State of California near the northwest corner of the intersection of Cedar and Manning Avenues. Buds from the sport were budded under my supervision at the above designated orchard into Nemaguard (unpatented) peach tree rootstocks, and the fruit and tree characteristics resulting from such budding were observed by me to be identical to those of the original sport.

SUMMARY OF THE NEW VARIETY

The instant variety of nectarine tree is characterized by the ripening of its fruit 10 to 14 days earlier than the fruit of the Armking variety under the growing conditions prevailing in the San Joaquin Valley of California. The new nectarine tree, which is of large size and vigorous growth, is further characterized by its bearing of clingstone, yellow-fleshed fruit which is more highly colored than the fruit borne by the Mayred nectarine tree having a blush of Arabian Red-Red Robin (page 37, plate 7, L-6) on a ground color of Golden Glow (page 41, plate 9, L-6).

BRIEF DESCRIPTION OF THE DRAWING

The accompanying drawing is a color photograph of four mature fruits of the subject variety, with two of the fruits divided on the suture plane to show the flesh color and the stone, together with a representative twig showing characteristic leaves.

DETAILED DESCRIPTION

Referring more specifically to the pomological details of this new and distinct variety of nectarine tree, the following has been observed under the ecological conditions prevailing in the designated orchard near Fowler, Calif. All major color code plate identifications are by reference to Maerz and Paul Dictionary of Color, Second Edition 1950.

TREE

Size: Large.

Figure: Spreading.

Productivity: Very productive.

Regularity of bearing: Regular bearer.

Trunk: Diameter in relation to length, stocky; surface character, smooth.

Branches: Size, large; surface character, smooth; color, grey 31 (page 53, plate 15, C-6); lenticels, numerous with size 1 × 5 mm.

Leaves:

- *Size.*—Large.
- *Length.*—150 mm. average.
- *Width.*—40 mm. average.
- *Shape.*—Oval-lanceolate, apex accuminate.
- *Color.*—Upperside, fir (page 71, plate 24, L-7); lowerside, lichen (page 69, plate 23, H-6).
- *Marginal Form.*—Finely serrate.
- *Petiole.*—Length 12 mm. average; diameter, 2 mm. average.
- *Glandular characteristics.*—Two to four, reniform, variable arrangement on both petiole and base of blade; color, chartreuse green (page 47, plate 12, L-2).

Flower buds: Size, medium to large; shape, obtuse to conical and plump; surface, pubescent.

Flowers:

- *Date of bloom.*—(As observed in 1976) First bloom, February 13; 90% open, March 1; petal fall, March 8.
- *Size.*—Large 30 mm. diameter.
- *Color.*—Upperside, thulite pink (page 123, plate 50, I-1); lowerside, thulite pink (page 123, plate 50, J-1).
- *Number of pistils and stamens.*—Pistils, 1; stamens, 37 to 42.

FRUIT

Maturity: 10 to 14 days before Armking (U.S. Plant Pat. No. 2,943).

Size:

- *Axial diameter.*—57 to 60 mm.

*Transverse in suture plane.*—60 to 62 mm.

*Transverse at right angles to suture plane.*—61 to 63 mm.

Form: Round, oblong, with unequal sides.

*Suture.*—Distinct, slightly depressed, deeper at apex, slight depression beyond pistil point.

*Ventral surface.*—Smooth.

*Stem cavity.*—Acute angles; medium width and depth, 20 mm. × 25 mm. × 12 mm. deep.

*Base.*—Shoulders rounded.

*Apex.*—Somewhat rounded and slightly depressed.

*Pistil point.*—Mucronate.

*Stem.*—Length, 10 mm.; caliper 4 mm.

Skin:

Thickness.—Medium.

*Texture.*—Medium.

*Tendency to crack.*—None observed.

*Color.*—Blush, Arabian Red-Red Robin (page 37, plate 7, L-6); ground color, Golden Glow (page 41, plate 9, L-6).

*Pubesence.*—None, smooth skin of nectarine.

Flesh:

*Color.*—Uniform with surface of pit cavity and pit well, Golden Glow (page 41, plate 9, L-6).

*Juice.*—Juicy.

*Flavor.*—Sweet, subacid, highly flavored and pleasing.

*Aroma.*—Pleasing and distinct.

*Texture.*—Fine grained, tender and melting.

*Ripening.*—Even.

*Eating quality.*—Good.

Stone: Cling.

*Size.*—Length, 30 mm. average; width, 20 mm. average.

*Form.*—Ovate, rather plump and pointed.

*Sides.*—A few shallow pits, irregular shallow grooves and small ridges.

*Sutures.*—Ventral, narrow and shallow grooved; dorsal, wide, deeply grooved and decidedly winged.

*Color.*—Leghorn (page 43, plate 10, D-3).

*Tendency to split.*—None.

Use: Fresh.

Keeping quality: Good.

Shipping quality: Good.

Although the new variety of nectarine tree possesses the described characteristics as a result of the growing conditions in Fresno County, Calif., in the central portion of the San Joaquin Valley, it is to be understood that variations of the usual magnitude in characteristics incident to growing conditions, fertilization, pruning, and pest control are to be expected.

Having thus described and illustrated my new variety of nectarine tree, what is new and desired to be secured by Letters Patent is:

1. A new and distinct variety of nectarine tree, substantially as illustrated and described, characterized by its vigorous growth and large size; its bearing of early ripening, very highly colored, clingstone, yellow fleshed fruit which ripens from 10 to 14 days earlier than the fruit of the Armking nectarine tree (U.S. Plant Pat. No. 2,943) and which is smoother, glossier and more highly colored than the fruit of the Mayred nectarine tree (U.S. Plant Pat. No. 2,758); and which is further distinguished from the Armking nectarine tree by its even more vigorous growth and more nearly spherical fruit.

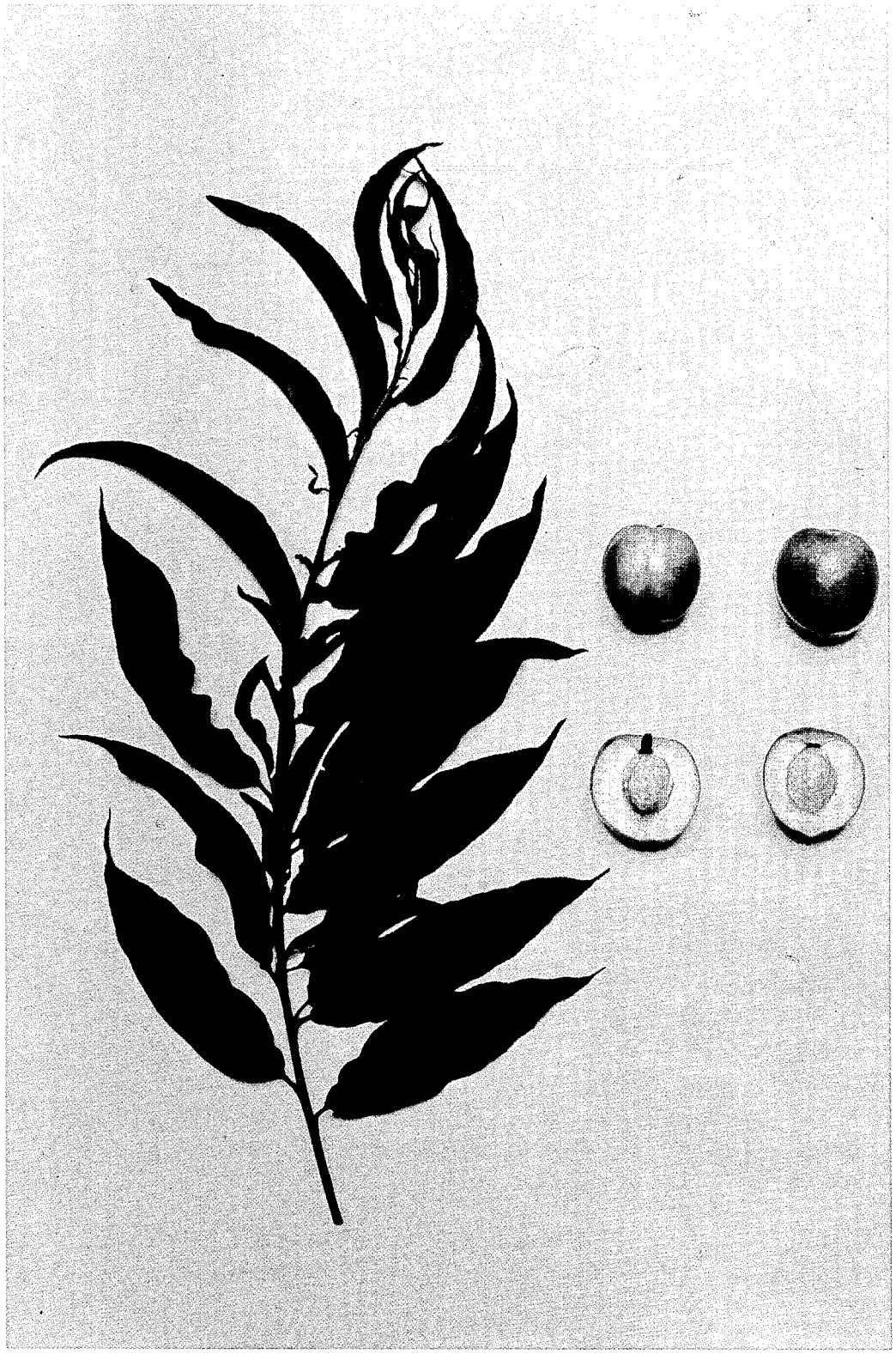

* * * * *